United States Patent [19]

Walder et al.

[11] Patent Number: 4,976,697
[45] Date of Patent: Dec. 11, 1990

[54] CATHETER OBTURATOR WITH AUTOMATIC FEED AND CONTROL

[75] Inventors: Anthony J. Walder, Franklin; Donald D. Solomon, Spring Valley; Richard W. Beck; James M. Lambert, both of Centerville, all of Ohio; Timothy Ignatius; Mark Crawford, both of Sandy, Utah

[73] Assignee: Becton, Dickinson and Company, Franklin Lakes, N.J.

[21] Appl. No.: 427,422

[22] Filed: Oct. 26, 1989

[51] Int. Cl.$^5$ .............................................. A61M 5/178
[52] U.S. Cl. ..................................... 604/164; 604/171
[58] Field of Search .................. 604/164, 171, 265, 53, 604/54

[56] References Cited

U.S. PATENT DOCUMENTS

| | | |
|---|---|---|
| 3,313,299 | 4/1967 | Spademan . |
| 3,703,174 | 11/1972 | Smith . |
| 3,727,613 | 4/1973 | Sorenson et al. . |
| 3,734,095 | 5/1973 | Santomieri . |
| 3,826,256 | 7/1974 | Smith . |
| 3,835,854 | 9/1974 | Jewett . |
| 3,838,688 | 10/1974 | May et al. . |
| 4,159,022 | 6/1979 | Pevsner . |
| 4,160,451 | 7/1979 | Chittenden . |
| 4,243,033 | 1/1981 | DeCaprio et al. . |
| 4,515,592 | 5/1985 | Frankhouser ..................... 604/171 |
| 4,696,296 | 9/1987 | Palmer ......................... 604/171 X |
| 4,834,710 | 5/1989 | Fleck ................................... 604/171 |

Primary Examiner—John D. Yasko
Attorney, Agent, or Firm—Robert P. Grindle

[57] ABSTRACT

An obturator is provided which allows for placing and withdrawing of a single catheter obturator over an extended period of time so as to allow speed intervals of use, and non-use of a catheter while in place in the patient's skin, while at the same time doing away with cumbersome, costly and time consuming administration and maintenance of saline and heparin locks. The device feeds the obturator in place for occluding the catheter lumen, when no fluids are being administered to the patient, and then may be retracted to a position allowing fluid feed through a supply tube connection to the catheter. The device includes a coating on the obturator rod which swells in contact with aqueous fluids to seal completely the catheter lumen which coating includes heparin to prevent clotting. Moreover, the entire internal functioning arrangement remains sterile during the entire period of use, thus avoiding infection.

20 Claims, 3 Drawing Sheets

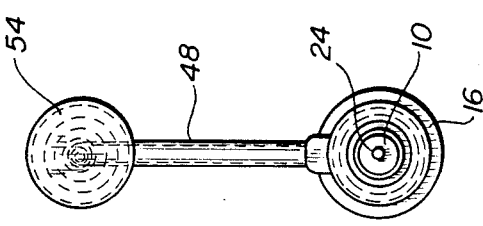
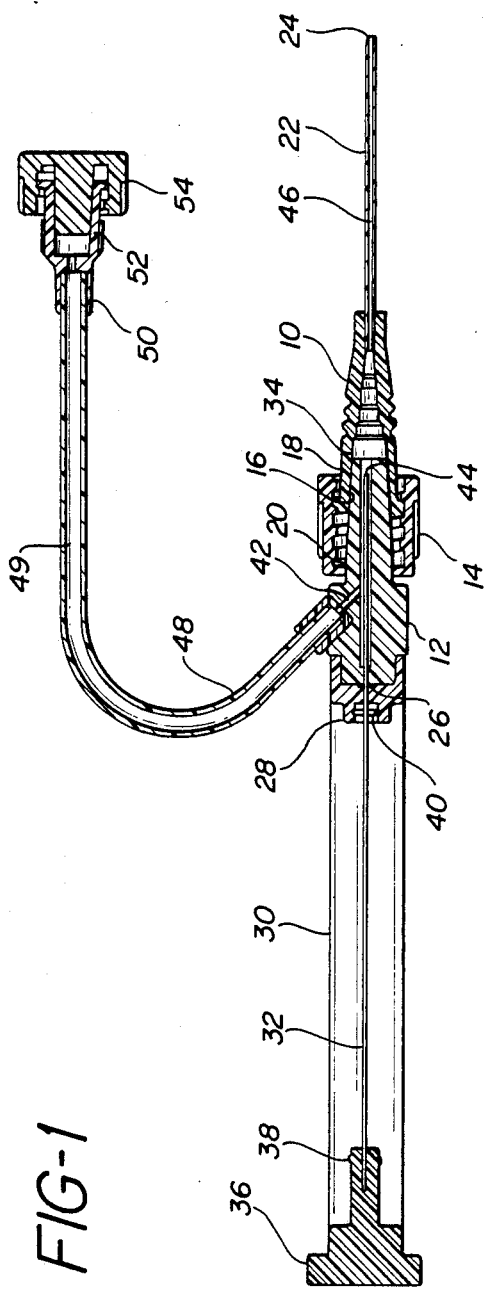
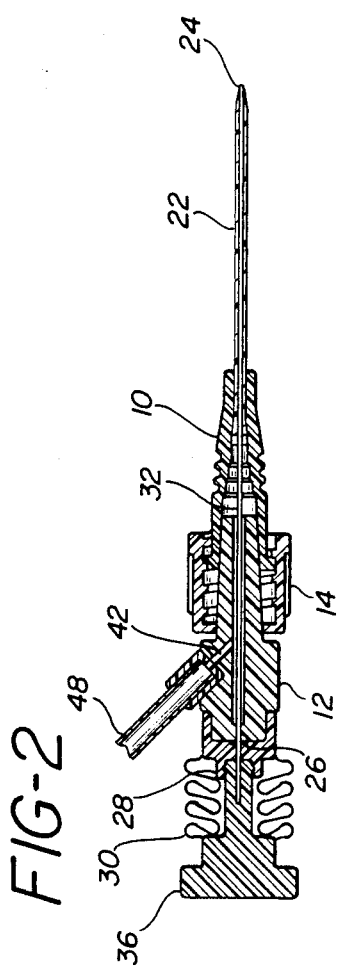

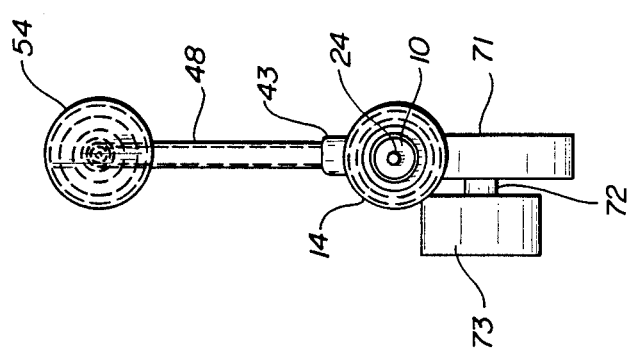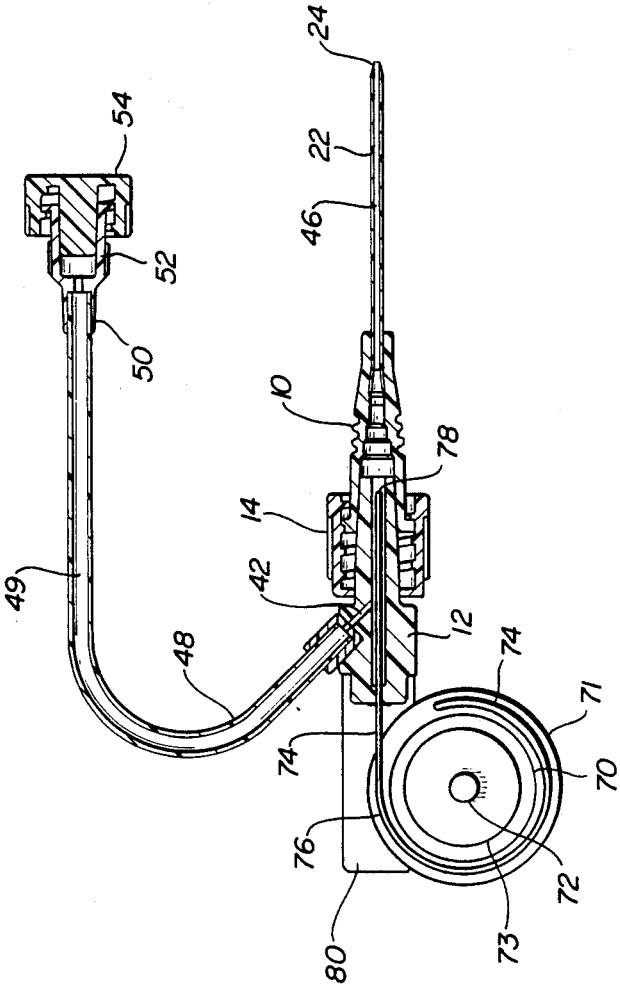

CATHETER OBTURATOR WITH AUTOMATIC FEED AND CONTROL

BACKGROUND AND STATEMENT OF THE INVENTION

This invention relates to catheterization of a patient, and more particularly to the control thereof so that the catheter may be used for a long period of time without the need for the usual and customary administration and maintenance of saline and heparin locks. More particularly, this invention relates to an obturator device which controls the lumen of the catheter, selectively, to allow spaced intervals of feeding and non-feeding of fluids through the catheter to the patient while the same catheter and the associated obturator remain in place, and under continuous sterile conditions.

The obturator of the invention may be fed selectively to occlude the catheter lumen and then may be withdrawn to a position allowing fluid delivery through the catheter to the patient. Thereafter, the same obturator may be fed forward to occlude the lumen again until such time as the next fluid delivery is required. With such an arrangement, the same catheter-obturator assembly may be used for periods as long as seventy-two (72) hours, for example.

For many applications, a catheter, after insertion into a patient may be maintained in place for periods up to two weeks or more. During this time, the medication changeovers may be alternated with periods when no solutions are being administered to the patient. It is essential that patency of the catheter be maintained during the changeover and non fluid administration periods.

As will be understood by practitioners in the art, patency of vascular access catheters, with or without an attached intravenous drip, are generally maintained in one of three ways. First, a sterile aliquot of heparin solution may be injected into the catheter. This method, often termed a heparin lock or flush, is costly since expensive heparin is required for long periods. Secondly, a sterile bolus may be used of normal saline solution injected into the catheter as an alternative to the heparin application. Both of these methods are done routinely and often. They have certain limitations, however, because of normal diffusion at the tip of the catheter, blood may replace infused heparin or saline solution with the result being loss of patency through the formation of a clot near the tip of the catheter.

Finally, maintenance of patency may be maintained by the use of a stainless steel or plastic obturator inserted loosely inside the catheter and attached with a luer connector. These devices are somewhat primitive, and do not completely seal the catheter so that blood may seep back into the space between the catheter and the obturator. This backflow of blood not only may clot and occlude the catheter or interfere with subsequent removal thereof, but also is an excellent breeding ground for infection.

With this invention, by contrast, a device is provided in the form of an elongated obturator comprised of a rod of semi-flexible material which may be fed through the use of, alternatively, a push rod arrangement or a reel feed arrangement to allow feeding of a sterile obturator into and through the lumen of an in-place catheter. In this connection, this invention is related to the invention taught and claimed in co-pending application Ser. No. 369,430, filed June 21, 1989 which is hereby incorporated by reference in its entirety.

That is, the invention claimed in that co-pending application describes and claims an obturator arrangement with a specific coating on the surface thereof for providing the proper degree of swelling necessary for an obturator as utilized in the device of this invention so as to seal completely the lumen of the catheter once the obturator is in place in its sealing position. Thus, the elongated slightly flexible obturator rod of the invention here utilizes on the surface thereof a coating comprised of a hydrophilic polyetherurethane capable of absorbing liquid and increasing the diameter of the obturator. Moreover, the coating includes an anti-thrombogenic and/or anti-infective agent bulk distributed in the polyetherurethane material. That is, the agents, whether anti-thrombogenic or anti-infective or both, are distributed throughout the polyetherurethane so that there is a slow release of these agents during use of the obturator of the invention.

When the obturator of the invention is fed forward into its sealing position in the lumen of the in-place catheter, it is wetted by an aqueous liquid such as blood, for example. The hydrophilic polyetherurethane absorbs the blood or other aqueous liquid causing it to expand so that the obturator overall dimension increases in diameter and contacts the lumen wall of the catheter to form a seal. Moreover, during this expansion, the anti-thrombogenic and/or anti-infective agent is slowly released in order to avoid infection and/or blood clotting.

Thereafter, the user may, with the device of the invention, withdraw the obturator from a position occluding the catheter lumen completely to a withdrawn position wherein a fluid delivery entry may be made into the catheter lumen for administering a fluid to a patient. Subsequently, in accordance with this invention, once the fluid has been delivered in the quantity desired, the fluid delivery outlet to the lumen may be stoppered and the same obturator, in accordance with this invention, may be fed forward again to reseal the catheter lumen until the next fluid delivery is to be made.

In considering generally the conditions for carrying out the invention here, the basic rod material upon which the hydrophilic polyetherurethane is coated may be any substantially non-hydrophilic material which, when extruded, is of sufficient stiffness in order to provide the control necessary during its use while being sufficiently flexible in order to be maneuvered, as will be discussed in more detail below. Suitable materials are, for example, metal, such as stainless steel, or preferably, a polymer. Preferred polymers for the rod are the polyolefins, such as polyethylene or polypropylene, and polytetrafluoroethylene, polyester, polyamide, polyurethane, polystyrene, polyvinyl chloride and liquid crystal polymers.

In the past, arrangements have been provided wherein catheters themselves have included a feeding device for moving the catheter in place. Moreover, insertion catheters have utilized controls for feeding a separate needle for actual insertion through the skin of the patient which needle is withdrawn from any further use once the catheter is in place. For example, U.S. Pat. No. 3,734,095 teaches placement of a stylet needle within a catheter prior to venipuncture and removal of the needle after the venipuncture. The device described deals with controlled insertion and withdrawal of the stylet. However, the system does not have any moveable parts. The system of the invention discloses a method of removal of the needle without exposing the luer of the catheter to air and/or contaminants with accessories. U.S. Pat. Nos. 3,313,299 and 3,727,613 also teach devices of this kind.

U.S. Pat. No. 3,835,854 teaches a device which feeds the catheter through the vein, as discussed above. The device uses friction to propel the catheter into the vein. U.S. Pat. No. 3,838,688 also uses a friction type of arrangement of this kind. By contrast with the invention here, the obturator rod is anchored, in one embodiment, to a reel acting as a cam which is then used to insert or withdraw the obturator rod, as required into the attached catheter.

Other U.S. patents teach inventions which insert a catheter into the vein of a patient by a pressure mechanism. This kind of device is taught in U.S. Pat. Nos. 4,159,022; 4,243,033; 3,703,174 and 3,826,256.

U.S. Pat. No. 4,160,451 uses a mechanism, also, for feeding a catheter into place in the vein of a patient. The point of the invention taught in this patent is to place the catheter so that it cannot be accidentally retracted.

With this invention by contrast, an obturator rod is fed into the already in place catheter for the purposes of occluding the lumen of the catheter, as desired, without having to use the conventional expensive and cumbersome procedures of heparin or saline locks. Moreover, the device of the invention is sterile when placed in use and remains sterile during the entire use procedure. In addition, the obturator rod when placed in its sealing position, seals effectively the lumen of the catheter from any blood leakage. It avoids contamination of any kind and any blood clotting because of the presence of the heparin and/or anti-infective agent in the swellable material coating the rod.

Other objects and advantages of this invention will be apparent from the following description, the accompanying drawings, and the appended claims.

DESCRIPTION OF THE DRAWINGS

FIG. 1 is a somewhat diagramatic longitudinal sectional view of one embodiment of the invention illustrating a feeding device for feeding an obturator rod into place for occluding an already in-place catheter, as desired, and for withdrawal of the obturator rod, as desired, for feeding fluid through the catheter, with the obturator rod shown in its withdrawn position;

FIG. 2 is a view of the device of FIG. 1 showing the obturator rod in its in-place position occluding the lumen of the catheter;

FIG. 3 is an end view of the device of FIG. 1 in elevation looking at the device from the right hand side thereof;

FIG. 6 is a somewhat diagramatic longitudinal sectional view of a further embodiment of an obturator rod feed device of the invention; and FIG. 7 is a view of the device of FIG. 6 in elevation as viewed from the right hand end thereof.

DETAILED DESCRIPTION OF THE INVENTION

Figure 4:
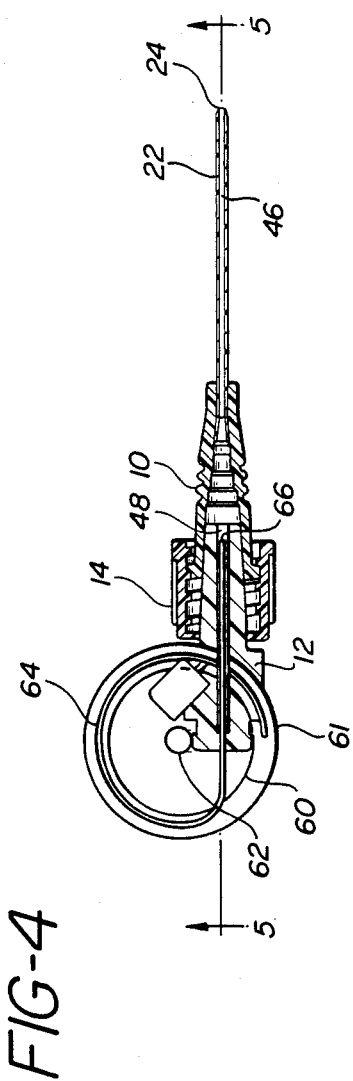
FIG. 4 is a somewhat diagramatic longitudinal sectional view of a further embodiment of the invention illustrating a reel feed arrangement for the obturator feeding device of the invention.

Referring to the drawings in which like reference characters refer to like parts throughout the several views thereof, FIG. 1 illustrates the invention as employed in a straight rod form of feed arrangement for the obturator rod of the invention. In FIG. 1, the main body 12 of the catheter arrangement is shown having a fluid passage 44 therethrough. The front end surface 18 of main body 12 is tapered to cooperate with the tapered surface 16 of the catheter body 10. A locking knob 14 is rotatable on main body 12 for joining the parts 10, 12 together along their cooperating tapered surfaces 16, 18, respectively. As a more secure connection, the rear end of the locking knob may have an edge as shown which moves into place over the abutment 20 on the outer surface of main body 12.

Extending forwardly from the catheter body 10 is the catheter 22 having a front end point 24 for insertion into the vein of a patient so as to communicate through lumen 46 of catheter 22 fluids fed to the catheter from a female luer connection 52 for feeding through the adapter 50 fluids to the lumen 49 of supply tube 48 for delivery of fluid through passage 42 to the passage 44 in main body 12. Cap 54 closes off female luer connection 52 until such time as a fluid supply is connected at which time the cap 54 is removed for such delivery.

Positioned in passage 44 is an obturator rod 32 which extends rearwardly out through an o-ring cap 28 having a sealing o-ring 26, to a snap cap 36 for manipulating and feeding the obturator rod 32 to and through the lumen 46 in catheter 22 in order to occlude completely lumen 46, as desired. Rod 32 is surrounded by a bellows type film sleeve 30 which collapses, as shown in FIG. 2, when cap 36 is moved to the right, as shown in FIG. 1 for moving the front end 34 of rod 32 forwardly into the lumen 46 of catheter 22.

That is, when it is desired to seal off the in-place opening 24 of catheter 22, cap 36 is moved to the right as shown in FIG. 1 until such time as the forward annular locking ring 38 of snap-cap 36 snaps into place in annular groove 40 in o-ring cap 28. When this happens, the front end portion, including point 34, of rod 32, because of the polyetherurethane coating on outer surface thereof, as discussed above, swells in contact with the aqueous environment of the blood in the vein of the patient because of the fact that the front end 24 of catheter 22 is in place in the vein of the patient. Also, because of the heparin incorporated into the polyetherurethane which is at this point swelling for cooperating in a sealing engagement with the inner diameter or inner walls of lumen 46 the heparin which is gradually and slowly released prevents any clot formation at the point 24. This positioning is shown clearly in FIG. 2. Of course, any anti-infective agent present in the coating will also be released.

Consequently, if a nurse or other technician desires to administer a fluid to the patient through catheter 22, the operator releases locking ring 38 from groove 40 and moves cap 36 to the left to a position which allows passage of fluid from supply tube 48 around the forward end of rod 32 in passage 44. At this time, cap 54 is removed and a male luer connection is inserted into female luer connection 52 with the male luer connection being connected to a supply of the fluid to be administered.

Figure 5:
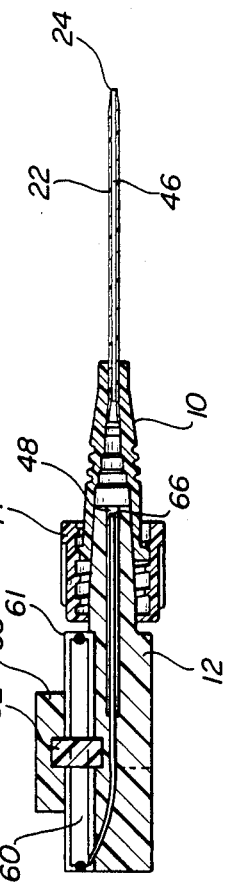
FIG. 5 is a sectional view of the device of FIG. 4 taken generally along lines 5—5 of FIG. 4.

FIGS. 4 and 5 show an additional embodiment of the invention here for feeding a coated obturator rod through lumen 46 of catheter 22. In this embodiment, a reel drive is utilized for feeding the obturator rod 64 through passage 48 and into lumen 46 of catheter 22. Reel 60 rotates around a shaft 62 in reel casing 61 for this purpose. As can be seen in FIG. 5, knob 68, positioned on one end of shaft 62, rotates reel 60 for feeding rod 64 through passage 48 into catheter 22 to the end 24 thereof. The front end 66 of rod 64 extends in the occluded position slightly out the front end 24 of catheter 22, in the same manner as front end 34 shown in FIG. 2.

FIGS. 6 and 7 show a further arrangement of reel drive device for feeding an obturator rod 74 through passage 48 for occluding lumen 46 of catheter 22 in the same manner as the previous embodiments. In this embodiment, reel 70 is rotated around a shaft 72 through the action of a knob 73. Obturator rod 74 moves, under this action, in either direction for either feeding the front end 78 of rod 74 to the right hand end of catheter 22 out and through lumen 46 of catheter 22 to a point where point 78 of rod 74 extends slightly out of the front end 24 of catheter 22. As can be seen in this embodiment, and particularly in the end view shown in FIG. 7, the axis of catheter 24 is at the same level as the feed portion of reel 70. In this connection, as shown in FIG. 6, reel casing 71 is supported and suspended from a support 80 for feeding rod 74 at the position 76 shown in FIG. 6. As will be understood, with rod 74 in the position shown in FIG. 6, fluids may be fed through the catheter lumen 46 from supply tube 48 and from luer connection 52.

It should be understood by practitioners-in-the-art that in molding plastic parts of the kind discussed here that molding design techniques may make it appropriate to combine two parts into a single molded part such as, for example, reel casing 71 and support 80, as shown in FIG. 6.

As discussed previously, in the extended position of rod 74 with the front end 78 extending slightly out the front end 24 of catheter 22, because of the coating of polyetherurethane, as discussed above, in contact with an aqueous environment, swelling takes place so that there is a cooperating seal between the internal walls of lumen 46 and the outer walls of swollen rod 74. Also, because of the anti-thrombogenic and/or anti-infective agent bulk distributed in the coating, there is a constant slow release of these agents in this environment in order to maintain patency of the in-dwelling catheter during several medication changeovers, while at the same time maintaining a sterile condition.

It should be understood that with each of the embodiments shown above, the main body 12 together with the catheter structure 22 itself and the fluid delivery structure 48, 50 are substantially the same with the only change being the actual feed mechanism for the obturator rod which may be selected among the several embodiments described.

In considering generally the conditions for carrying out the most enhanced results in connection herewith, which conditions have already been specifically discussed above and in connection with the above referred to co-pending application, the dimension of the obturator rod of the invention depends upon the dimension of the catheter being used in combination therewith. For example, for a rod used in conjunction with a 20 gauge catheter the diameter of the rod will be within the range of between about 0.005 and 0.028 inches, preferably 0.022 and 0.026 inches.

Most preferably, the tip for the rod has a diameter of 0.023 and is about 0.25 inches long with the remaining portion of the rod being 0.026 inches in diameter.

The coating on the swollen rod increases the rod dimensions described above within the range of between about 0.002 and 0.027 inches, and preferably within the range of between about 0.003 and 0.008 inches and most preferably 0.004 inches. Obviously, when the rod swells, the dimension of the rod with the coating increases and this has been found to be approximately an increase of one-half the thickness of the coating in place prior to any swelling.

With a 16 gauge catheter, the preferred rod dimension is within the range of between about 0.040 and 0.050 inches with a similar coating dimension as described above.

As a further treatment of the obturator rod and associated feeding device of the invention, the device is sterilized by gamma irradiation or ethylene oxide. It is placed in position for use as a sterile device since it will only be exposed to body fluids. The only way that it may become non-sterile would be with an exposure to contaminated infusates or from exposure to bacteremic blood.

Representative materials which may be used for the reel body include rigid polyvinyl chloride as the preferred material. Alternative materials include acrylonitrile-butadiene-styrene terpolymer, styrene, polycarbonate or polyacrylate. The reel body may be transparent for observing the feed movement of the rod. However, it may also be comprised of a colored or opaque material. The bellows film sleeve 30 shown in the embodiment of FIG. 1 may be comprised of, for example, polyethylene, polypropylene, polyvinyl chloride or polyesters. As an alternative to the bellows form of sleeve, a telescoping sleeve (not shown) may be provided comprised of a rigid polymer such as polystyrene.

Whereas, as discussed above, specific embodiments of obturator rod feed devices and associated connections have been shown, it should be understood that it is within the purview of this invention to provide other forms of feed arrangements or positioning of a reel feed, for example, connected to the main body of the catheter. That is, the axis of the reel body for feeding the obturator rod may be positioned in several different placements around the axis of the catheter itself.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. An obturator rod and associated feeding arrangement therefor for feeding the obturator rod selectively into and out of the occluded position in the lumen of an in-place catheter, while maintaining sterile conditions, comprising
   (a) an elongated semi-flexible obturator rod;
   (b) said obturator rod having a first end and a second end;
   (c) an obturator rod feed device positioned adjacent said obturator rod first end;
   (d) said obturator rod feed device having
      (1) a feed device body;

(2) said feed device body having a first end and a second end;

(3) said feed device body having an obturator rod passage extending from said first end to said second end;

(4) said feed device body second end for connection to the main body of an in-place catheter;

(5) said obturator rod passage in flow communication with an in-place catheter lumen of an in-place catheter connected to said main body of said obturator feed device body;

(6) means for feeding said obturator rod;

(7) said feeding means positioned on said first end of said feed device body;

(8) said feeding means including an obturator rod mover;

(9) said obturator rod mover connected to said first end of said obturator rod;

(10) said obturator rod mover for moving said second end of said obturator rod from a first position occluding the lumen of a catheter connected to said obturator rod feed device body to a second position allowing fluid through the lumen of a catheter connected to said obturator rod feed device body;

(11) sealing means on said feeding means for sealing said obturator rod from exposure in said first position or said second position; and (e) a hydrophilic polymer coating on said obturator rod;

(f) said hydrophilic polymer capable of absorbing a liquid and expanding to seal to the lumen wall of an in-place catheter in the first position of said obturator rod second end.

2. The device of claim 1, wherein said obturator rod mover comprises (a) a snap cap positioned on said first end of said obturator rod;

(b) cooperating locking means on said snap cap and said obturator rod feed device body first end; and (c) said sealing means is a foldable sleeve extending from said snap cap to said first end of said obturator rod feed device body for covering and maintaining said obturator rod sterile in said first and second position thereof.

3. The device of claim 1, wherein said obturator rod mover comprises (a) a feeding reel positioned on said obturator rod feed device body adjacent said first end thereof;

(b) said obturator rod first end being connected to said feeding reel; and (c) a portion of said obturator rod being wound around said feeding reel;

(d) whereby rotating said reel causes said second end of said obturator rod to move from said first position to said second position, and vice versa.

4. The device of claim 3 wherein said obturator rod mover comprises (a) a reel casing;

(b) said feeding reel positioned in said reel casing, and (c) said reel casing and said feed device body are integral.

5. The device of claim 3, wherein (a) said sealing means is said reel and the connection between the said adjacent obturator rod feed device body.

6. The device of claim 3, wherein (a) the axis of said obturator rod at the point where said obturator rod extends from said reel to said obturator rod feed device body is coaxial with the lumen of an in-place catheter connected to said second end of said obturator rod feed device body.

7. The device of claim 1, wherein (a) said hydrophilic polymer is polyether urethane.

8. The device of claim 1, wherein (a) said obturator rod is comprised of a material selected from the group consisting of stainless steel, polyethylene, polypropylene, polytetrafluoroethylene, polyester, polyamide, polyurethane, polystyrene, polyvinyl chloride, liquid crystal polymers, and mixtures thereof.

9. The device of claim 1

(a) wherein said coating has a medicinal agent bulk distributed therein; and (b) said medicinal agent being released when said coating absorbs a liquid and swells.

10. The device of claim 9, (a) wherein said medicinal agent is selected from the group consisting of an anti-infective agent, an antibiotic agent, and an anti-thrombogenic agent, and mixtures thereof.

11. A catheter assembly for maintaining an infusion catheter in-place over a period of time, said assembly including an obturator rod and associated feeding arrangement therefor for feeding the obturator rod selectively into and out of the occluded position in the lumen of the said in-place catheter, while maintaining sterile conditions, comprising (a) an infusion catheter;

(b) said catheter having a first end and a second end;

(c) a catheter main body connected to said catheter first end;

(d) said second end of said catheter for insertion into the blood vessel of a patient;

(e) a lumen extending through said catheter main body and said catheter;

(f) an elongated semi-flexible obturator rod;

(g) said obturator rod having a first end and a second end;

(h) an obturator rod feed device positioned adjacent said obturator rod first end;

(i) said obturator rod feed device having (1) a feed device body;

(2) said feed device body having a first end and a second end;

(3) said feed device body having an obturator rod passage extending from said first end to said second end;

(4) said feed device body second end connected to said catheter main body;

(5) said obturator rod passage in flow communication with said catheter lumen of said catheter connected to said main body of said obturator feed device body;

(6) means for feeding said obturator rod;

(7) said feeding means positioned on said first end of said feed device body;

(8) said feeding means including an obturator rod mover;

(9) said obturator rod mover connected to said first end of said obturator rod;

(10) said obturator rod mover for moving said second end of said obturator rod from a first position occluding said lumen of said catheter connected to said obturator rod feed device body to a second position allowing fluid through said lumen of said catheter connected to said obturator rod feed device body;

(11) sealing means on said feeding means for sealing said obturator rod from exposure in said first position or said second disposition; and (j) a hydrophilic polymer coating on said obturator rod;

(k) said hydrophilic polymer capable of adsorbing a liquid and expanding to seal to said lumen wall of said catheter in the first position of said obturator rod second end.

12. The device of claim 11, wherein said obturator rod mover comprises
   (a) a snap cap positioned on said first end of said obturator rod;
   (b) cooperating locking means on said snap cap and said obturator rod feed device body first end; and
   (c) said sealing means is a foldable sleeve extending from said snap cap to said first end of said obturator rod feed device body for covering and maintaining said obturator rod sterile in said first and second position thereof.

13. The device of claim 11, wherein said obturator rod mover comprises
   (a) a feeding reel positioned on said obturator rod feed device body adjacent said first end thereof;
   (b) said obturator rod first end being connected to said feeding reel; and
   (c) a portion of said obturator rod being wound around said feeding reel;
   (d) whereby rotating said reel causes said second end of said obturator rod to move from said first position to said second position, and vice versa.

14. The device of claim 13, wherein
   (a) said sealing means is said reel and the connection between the said adjacent obturator rod feed device body.

15. The device of claim 13, wherein
   (a) the axis of said obturator rod at the point where said obturator rod extends from said reel to said obturator rod feed device body is coaxial with the lumen of an in-place catheter connected to said second end of said obturator rod feed device body.

16. The device of claim 11, wherein
   (a) said hydrophilic polymer is polyether urethane.

17. The device of claim 11, wherein
   (a) said obturator rod is comprised of a material selected from the group consisting of stainless steel, polyethylene, polypropylene, polytetrafluoroethylene, polyester, polyamide, polyurethane, polystyrene, polyvinyl chloride, liquid crystal polymers, and mixtures thereof.

18. The device of claim 11
   (a) wherein said coating has a medicinal agent bulk distributed therein; and
   (b) said medicinal agent being released when said coating absorbs a liquid and swells.

19. The device of claim 18
   (a) wherein said medicinal agent is selected from the group consisting of an anti-infective agent, an antibiotic agent, and an anti-thrombogenic agent, and mixtures thereof.

20. The device of claim 11
   (a) wherein said feed device body and said feeding means are integral.

* * * * *